US009111016B2

(12) United States Patent  
Besson et al.

(10) Patent No.: US 9,111,016 B2
(45) Date of Patent: Aug. 18, 2015

(54) MANAGEMENT OF LIVE REMOTE MEDICAL DISPLAY

(75) Inventors: Guy Besson, Broomfield, CO (US); Jeffrey M. Garibaldi, St. Louis, MO (US)

(73) Assignee: STEREOTAXIS, INC., St. Louis, MO (US)

( * ) Notice: Subject to any disclaimer, the term of this patent is extended or adjusted under 35 U.S.C. 154(b) by 1893 days.

(21) Appl. No.: 12/168,790

(22) Filed: Jul. 7, 2008

(65) Prior Publication Data

US 2009/0012821 A1    Jan. 8, 2009

Related U.S. Application Data

(60) Provisional application No. 60/948,311, filed on Jul. 6, 2007.

(51) Int. Cl.
| G06F 19/00 | (2011.01) |
| G06Q 50/24 | (2012.01) |
| G09B 5/06 | (2006.01) |
| G09B 23/28 | (2006.01) |
| H04N 21/2365 | (2011.01) |
| H04N 21/2385 | (2011.01) |
| H04N 21/2665 | (2011.01) |
| H04N 21/431 | (2011.01) |
| H04N 21/434 | (2011.01) |
| H04L 29/06 | (2006.01) |

(52) U.S. Cl.
CPC .............. *G06F 19/321* (2013.01); *G06Q 50/24* (2013.01); *G09B 5/065* (2013.01); *G09B 23/28* (2013.01); *H04L 65/602* (2013.01); *H04L 65/80* (2013.01); *H04N 21/2365* (2013.01); *H04N 21/2385* (2013.01); *H04N 21/2665* (2013.01); *H04N 21/4312* (2013.01); *H04N 21/4314* (2013.01); *H04N 21/4347* (2013.01); *G06F 19/327* (2013.01)

(58) Field of Classification Search
None
See application file for complete search history.

(56) References Cited

U.S. PATENT DOCUMENTS

| 5,654,864 A | 8/1997 | Ritter et al. |
| 5,909,244 A * | 6/1999 | Waxman et al. ........... 348/222.1 |
| 5,931,818 A | 8/1999 | Werp et al. |
| 5,993,001 A | 11/1999 | Bursell et al. ................. 351/212 |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |

(Continued)

OTHER PUBLICATIONS

Volk, Andy "Video Compression: A Codec Primer." Oct. 22, 2004.*
Fritts, Jason "Multi-Level Memory Prefetching for Media and Stream Processing." Washington University, Department of Computer Science, Aug. 28, 2002.*

(Continued)

*Primary Examiner* — Neal Sereboff
(74) *Attorney, Agent, or Firm* — Harness, Dickey & Pierce, P.L.C.

(57) ABSTRACT

A system and method of locally displaying multiple items of medical information from at least one remote medical system having an output display. The method includes assembling the multiple items of medical information from the output display of at least one remote medical systems into a composite display having regions corresponding to the multiple items of medical information. Video data for the composite display is communicated over a network to a local display. Video data corresponding to the regions of the display are treated differently to provide a composite display with regions of different image quality.

5 Claims, 7 Drawing Sheets

(56) References Cited

U.S. PATENT DOCUMENTS

| | | | |
|---|---|---|---|
| 6,157,853 A | 12/2000 | Blume et al. | |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,315,709 B1 | 11/2001 | Garibaldi et al. | |
| 6,330,467 B1 | 12/2001 | Creighton, IV et al. | |
| 6,352,363 B1 | 3/2002 | Munger et al. | |
| 6,364,823 B1 | 4/2002 | Garibaldi et al. | |
| 6,375,606 B1 | 4/2002 | Garibaldi et al. | |
| 6,385,472 B1 | 5/2002 | Hall et al. | |
| 6,401,723 B1 | 6/2002 | Garibaldi et al. | |
| 6,428,551 B1 | 8/2002 | Hall et al. | |
| 6,459,924 B1 | 10/2002 | Creighton, IV et al. | |
| 6,475,223 B1 | 11/2002 | Werp et al. | |
| 6,505,062 B1 | 1/2003 | Ritter et al. | |
| 6,507,751 B2 | 1/2003 | Blume et al. | |
| 6,522,909 B1 | 2/2003 | Garibaldi et al. | |
| 6,524,303 B1 | 2/2003 | Garibaldi | |
| 6,527,782 B2 | 3/2003 | Hogg et al. | |
| 6,537,196 B1 | 3/2003 | Creighton, IV et al. | |
| 6,542,766 B2 | 4/2003 | Hall et al. | |
| 6,562,019 B1 | 5/2003 | Sell | |
| 6,630,879 B1 | 10/2003 | Creighton, IV et al. | |
| 6,662,034 B2 | 12/2003 | Segner et al. | |
| 6,677,752 B1 | 1/2004 | Creighton, IV et al. | |
| 6,702,804 B1 | 3/2004 | Ritter et al. | |
| 6,733,511 B2 | 5/2004 | Hall et al. | |
| 6,755,816 B2 | 6/2004 | Ritter et al. | |
| 6,817,364 B2 | 11/2004 | Garibaldi et al. | |
| 6,834,201 B2 | 12/2004 | Gillies et al. | |
| 6,902,528 B1 | 6/2005 | Garibaldi et al. | |
| 6,911,026 B1 | 6/2005 | Hall et al. | |
| 6,940,379 B2 | 9/2005 | Creighton | |
| 6,968,846 B2 | 11/2005 | Viswanathan | |
| 6,975,197 B2 | 12/2005 | Creighton, IV | |
| 6,980,843 B2 | 12/2005 | Eng et al. | |
| 7,008,418 B2 | 3/2006 | Hall et al. | |
| 7,010,338 B2 | 3/2006 | Ritter et al. | |
| 7,019,610 B2 | 3/2006 | Creighton, IV et al. | |
| 7,020,512 B2 | 3/2006 | Ritter et al. | |
| 7,066,924 B1 | 6/2006 | Garibaldi et al. | |
| 7,137,976 B2 | 11/2006 | Ritter et al. | |
| 7,161,453 B2 | 1/2007 | Creighton, IV | |
| 7,189,198 B2 | 3/2007 | Harburn et al. | |
| 7,190,819 B2 | 3/2007 | Viswanathan | |
| 7,211,082 B2 | 5/2007 | Hall et al | |
| 7,248,914 B2 | 7/2007 | Hastings et al. | |
| 7,264,584 B2 | 9/2007 | Ritter et al. | |
| 7,376,907 B2* | 5/2008 | Santoro et al. | 715/765 |
| 2001/0038683 A1 | 11/2001 | Ritter et al. | |
| 2002/0019644 A1 | 2/2002 | Hastings et al. | |
| 2002/0100486 A1 | 8/2002 | Creighton, IV et al. | |
| 2002/0177789 A1 | 11/2002 | Ferry et al. | |
| 2003/0125752 A1 | 7/2003 | Werp et al. | |
| 2004/0006301 A1 | 1/2004 | Sell et al. | |
| 2004/0019447 A1 | 1/2004 | Shachar | |
| 2004/0030244 A1 | 2/2004 | Garibaldi et al. | |
| 2004/0054760 A1* | 3/2004 | Ewing et al. | 709/219 |
| 2004/0064153 A1 | 4/2004 | Creighton, IV et al. | |
| 2004/0068173 A1 | 4/2004 | Viswanathan | |
| 2004/0133130 A1 | 7/2004 | Ferry et al. | |
| 2004/0147829 A1 | 7/2004 | Segner et al. | |
| 2004/0157082 A1 | 8/2004 | Ritter et al. | |
| 2004/0158972 A1 | 8/2004 | Creighton, IV et al. | |
| 2004/0186376 A1 | 9/2004 | Hogg et al. | |
| 2004/0249262 A1 | 12/2004 | Werp et al. | |
| 2004/0249263 A1 | 12/2004 | Creighton, IV | |
| 2004/0260172 A1 | 12/2004 | Ritter et al. | |
| 2004/0267106 A1 | 12/2004 | Segner et al. | |
| 2005/0004585 A1 | 1/2005 | Hall et al. | |
| 2005/0020911 A1 | 1/2005 | Viswanathan et al. | |
| 2005/0021063 A1 | 1/2005 | Hall et al. | |
| 2005/0033162 A1 | 2/2005 | Garibaldi et al. | |
| 2005/0043611 A1 | 2/2005 | Sabo et al. | |
| 2005/0065435 A1 | 3/2005 | Rauch et al. | |
| 2005/0096589 A1 | 5/2005 | Shachar | |
| 2005/0113628 A1 | 5/2005 | Creighton, IV et al. | |
| 2005/0113812 A1 | 5/2005 | Viswanathan et al. | |
| 2005/0119556 A1 | 6/2005 | Gillies et al. | |
| 2005/0119687 A1 | 6/2005 | Dacey et al. | |
| 2005/0182315 A1 | 8/2005 | Ritter et al. | |
| 2005/0203390 A1* | 9/2005 | Torp et al. | 600/437 |
| 2005/0256398 A1 | 11/2005 | Hastings et al. | |
| 2005/0273130 A1 | 12/2005 | Sell | |
| 2006/0004382 A1 | 1/2006 | Hogg et al. | |
| 2006/0009735 A1 | 1/2006 | Viswanathan et al. | |
| 2006/0025676 A1 | 2/2006 | Viswanathan et al. | |
| 2006/0025679 A1 | 2/2006 | Viswanathan et al. | |
| 2006/0025719 A1 | 2/2006 | Viswanathan et al. | |
| 2006/0036125 A1 | 2/2006 | Viswanathan et al. | |
| 2006/0036163 A1 | 2/2006 | Viswanathan | |
| 2006/0036213 A1 | 2/2006 | Viswanathan et al. | |
| 2006/0041178 A1 | 2/2006 | Viswanathan et al. | |
| 2006/0041179 A1 | 2/2006 | Viswanathan et al. | |
| 2006/0041180 A1 | 2/2006 | Viswanathan et al. | |
| 2006/0041181 A1 | 2/2006 | Viswanathan et al. | |
| 2006/0041245 A1 | 2/2006 | Ferry et al. | |
| 2006/0058646 A1 | 3/2006 | Viswanathan | |
| 2006/0061445 A1 | 3/2006 | Creighton, IV et al. | |
| 2006/0074297 A1 | 4/2006 | Viswanathan | |
| 2006/0079745 A1 | 4/2006 | Viswanathan | |
| 2006/0079812 A1 | 4/2006 | Viswanathan | |
| 2006/0094956 A1 | 5/2006 | Viswanathan | |
| 2006/0100505 A1 | 5/2006 | Viswanathan | |
| 2006/0114088 A1 | 6/2006 | Shachar | |
| 2006/0116633 A1 | 6/2006 | Shachar | |
| 2006/0144407 A1 | 7/2006 | Aliberto et al. | |
| 2006/0144408 A1 | 7/2006 | Ferry | |
| 2006/0145799 A1 | 7/2006 | Creighton, IV | |
| 2006/0270915 A1 | 11/2006 | Ritter et al. | |
| 2006/0270948 A1 | 11/2006 | Viswanathan et al. | |
| 2006/0278248 A1 | 12/2006 | Viswanathan | |
| 2007/0016010 A1 | 1/2007 | Creighton, IV et al. | |
| 2007/0016131 A1 | 1/2007 | Munger et al. | |
| 2007/0019330 A1 | 1/2007 | Wolfersberger | |
| 2007/0021731 A1 | 1/2007 | Garibaldi et al. | |
| 2007/0021742 A1 | 1/2007 | Viswanathan | |
| 2007/0021744 A1 | 1/2007 | Creighton, IV | |
| 2007/0030958 A1 | 2/2007 | Munger | |
| 2007/0032746 A1 | 2/2007 | Sell | |
| 2007/0038064 A1 | 2/2007 | Creighton, IV | |
| 2007/0038065 A1 | 2/2007 | Creighton, IV et al. | |
| 2007/0038074 A1 | 2/2007 | Ritter et al. | |
| 2007/0038410 A1 | 2/2007 | Tunay | |
| 2007/0040670 A1 | 2/2007 | Viswanathan | |
| 2007/0043455 A1 | 2/2007 | Viswanathan et al. | |
| 2007/0049909 A1 | 3/2007 | Munger | |
| 2007/0055124 A1 | 3/2007 | Viswanathan et al. | |
| 2007/0055130 A1 | 3/2007 | Creighton, IV | |
| 2007/0060829 A1 | 3/2007 | Pappone | |
| 2007/0060916 A1 | 3/2007 | Pappone | |
| 2007/0060962 A1 | 3/2007 | Pappone | |
| 2007/0060966 A1 | 3/2007 | Pappone | |
| 2007/0060992 A1 | 3/2007 | Pappone | |
| 2007/0062546 A1 | 3/2007 | Viswanathan et al. | |
| 2007/0062547 A1 | 3/2007 | Pappone | |
| 2007/0073288 A1 | 3/2007 | Hall et al. | |
| 2007/0088197 A1 | 4/2007 | Garibaldi et al. | |
| 2007/0135804 A1 | 6/2007 | Ritter | |
| 2007/0137656 A1 | 6/2007 | Viswanathan | |
| 2007/0146106 A1 | 6/2007 | Creighton, IV | |
| 2007/0149946 A1 | 6/2007 | Viswanathan | |
| 2007/0159457 A1 | 7/2007 | Arthur | 345/156 |
| 2007/0161882 A1 | 7/2007 | Pappone | |
| 2007/0167720 A1 | 7/2007 | Viswanathan | |
| 2007/0179492 A1 | 8/2007 | Pappone | |
| 2007/0197899 A1 | 8/2007 | Ritter et al. | |
| 2007/0197901 A1 | 8/2007 | Viswanathan | |
| 2007/0197906 A1 | 8/2007 | Ritter | |
| 2007/0225589 A1 | 9/2007 | Viswanathan | |
| 2007/0250041 A1 | 10/2007 | Werp | |

(56) References Cited

U.S. PATENT DOCUMENTS

| | | |
|---|---|---|
| 2007/0270686 A1 | 11/2007 | Ritter et al. |
| 2008/0004595 A1 | 1/2008 | Viswanathan |
| 2008/0006280 A1 | 1/2008 | Aliberto et al. |
| 2008/0015427 A1 | 1/2008 | Kastelein et al. ............. 600/410 |
| 2008/0015670 A1 | 1/2008 | Pappone ...................... 607/122 |
| 2008/0016677 A1 | 1/2008 | Creighton, IV |
| 2008/0016678 A1 | 1/2008 | Creighton, IV et al. |
| 2008/0021326 A1* | 1/2008 | Bakircioglu et al. ......... 600/454 |
| 2008/0039705 A1 | 2/2008 | Viswanathan |
| 2008/0039830 A1 | 2/2008 | Munger et al. |
| 2008/0047568 A1 | 2/2008 | Ritter et al. |
| 2008/0055239 A1* | 3/2008 | Garibaldi et al. ............. 345/156 |
| 2008/0058608 A1 | 3/2008 | Garibaldi et al. |
| 2008/0058609 A1 | 3/2008 | Garibaldi et al. |
| 2008/0058963 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0064969 A1 | 3/2008 | Kastelein |
| 2008/0065061 A1 | 3/2008 | Viswanathan |
| 2008/0077007 A1 | 3/2008 | Hastings et al. |
| 2008/0092993 A1 | 4/2008 | Creighton, IV |
| 2008/0097200 A1 | 4/2008 | Blume et al. |
| 2008/0114335 A1 | 5/2008 | Flickinger et al. |
| 2008/0294232 A1 | 11/2008 | Viswanathan |

OTHER PUBLICATIONS

Geisler et al., "A real-time foveated multiresolution system for low-bandwidth video communication" SPIE Proceedings, vol. 3299, 1998.*

Huang, et al., "A Hybrid Spatial-Temporal Fine Granlular Scalable Coding for Adaptive QoS Internet Video" Proceedings of the 2005, $31^{st}$ EUROMICRO Conference on Software Engineering and Advanced Applications 2005.*

Nguyen, "Streaming and Congestion Control using Scalable Video Coding based on H.264/AVC" University Hannover Jun. 2006.*

Maxim "Bandwisdth Versus Video Resolution" May 2001.*

Wiebe et al., "The Technology—Key Concepts" Dec. 2001.*

Definition—"look at" thefreedictionary.com as downloaded Jan. 10, 2012.*

Definition—"phrasal verb" thefreedictionary.com as downloaded Jan. 10, 2012.*

Magnetic Manipulation Instrumentation for Medical Physics Research Authors: G. T. Gillies, r. C. Ritter, W. C. Broaddus, M. S. Grady, M. A. Howard, III, R. G. McNeil 1994 American Institute of Physics Rev. Sci. Instrum. vol. 65, No. 3, Mar. 1994 pp. 533-562.

International Search Report and Written Opinion for corresponding PCT/US08/069354 Date: Sep. 3, 2008 pp. 11.

* cited by examiner

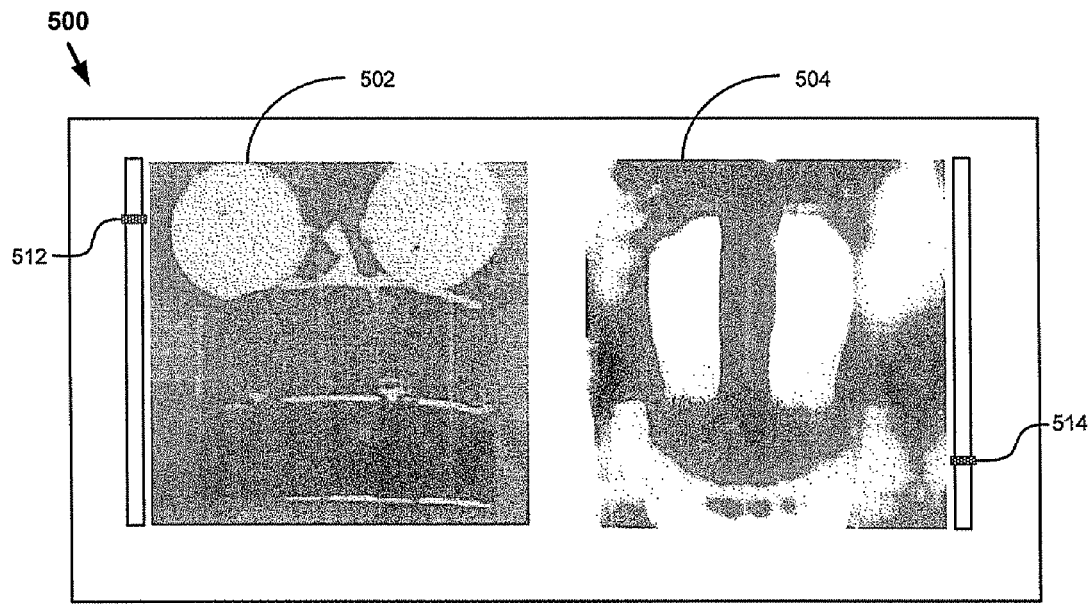
FIG. 5-A
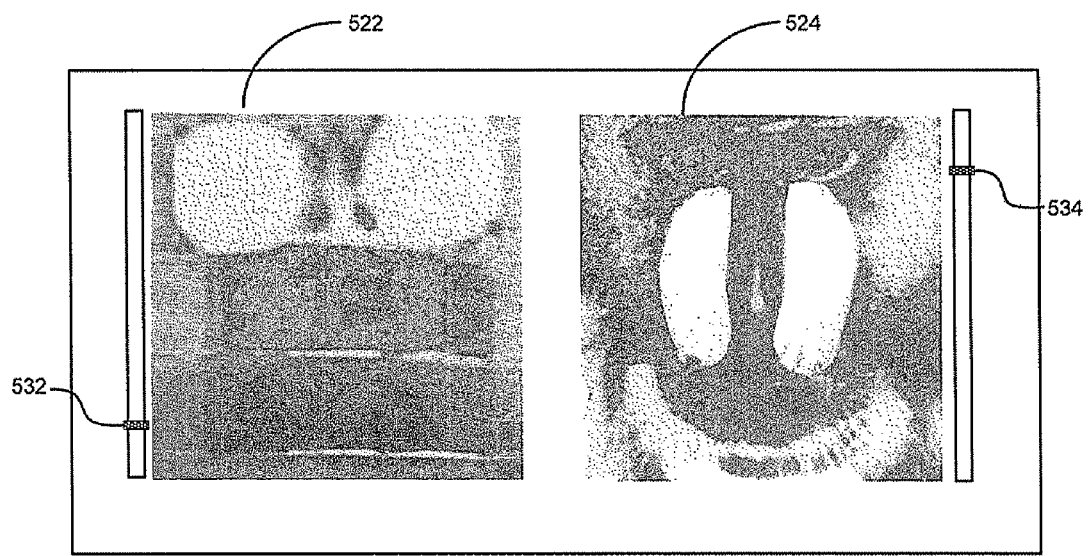
FIG. 5-B

MANAGEMENT OF LIVE REMOTE MEDICAL DISPLAY

CROSS-REFERENCE TO RELATED APPLICATIONS

This application claims priority to U.S. Provisional Patent Application Ser. No. 60/948,311, filed Jul. 6, 2007. The disclosure of the above-referenced application is incorporated herein by reference.

FIELD OF THE INVENTION

This invention relates to methods and systems for managing one or more live remote medical displays. In particular, a method is disclosed for the management of network bandwidth for network connections between a composite display system workstation and several remote field workstations.

BACKGROUND OF THE INVENTION

The evolution of medicine, and in particular, of interventional medicine, has led to the development of complex systems integrating patient monitoring sub-systems, imaging systems encompassing several modalities such as x-ray, MRI, ultrasound, nuclear medicine, and optical systems providing various close views of the anatomy being operated on. Additional sub-systems are often required, depending on the specifies of a given medical intervention. As an example, ablation means are often employed in the treatment of various lesions.

Within the field of interventional medicine, the recent trend has been toward the development and deployment of minimally invasive intervention systems include navigation systems, such as the Niobe™ magnetic navigation system developed by Stereotaxis, St. Louis, Mo. Such systems typically comprise an imaging means for real-time guidance and monitoring of the intervention; additional feedback is provided by a three-dimensional (3D) localization system that allows real-time determination of the catheter or interventional device tip position and orientation with respect to the operating room and, through co-registered imaging, with respect to the patient.

As a more specific example of complex interventions only recently made possible, the availability of methods and systems for safe, efficient minimally invasive interventions have greatly impacted and changed the practice of cardiac treatment delivery in the last decade. The treatment of a number of cardiac disorders has become possible without requiring open heart surgery. In particular, minimally invasive vascular and chamber navigation devices and systems have evolved to the point that a great number of heart conditions, such as electrical disorders of the heart rhythm, and arterial-related conditions, such as angina pectoris and heart tissue ischemia, can now be diagnosed and treated through the insertion and navigation of thin elongated devices through an arterial or venous incision and to the region of interest.

As methods and technologies evolve, the range and complexity of conditions amenable to minimally invasive diagnosis and treatment has increased. As a specific example, the field of medical device endo-lumen and endocardiac navigation is greatly specialized, and experts need mastery of disciplines at the cross-road of science, medicine, and engineering to bring about the best outcomes. Due to the risks intrinsic to cardiac surgery and similar procedures, the availability of training and teaching tools, the capability to remotely attend live interventions, and the tools required to allow a remote user to take control of an intervention, are key in the development of the next generation of practitioners and the safe and effective performance of complex operations.

Technology has been developed to enable physicians, call center representatives, and other attendant staff to remotely access multiple live, high resolution displays necessary to monitor and perform medical procedures. Each display and associated controls presents image or other graphic or text data relevant to a sub-system, and a user-interface (UIF) associated with that display enables control of that sub-system. One of the technology evolution challenges is to find a way to remotely view a number of high refresh rate, high resolution medical displays via a network with reasonable bandwidth requirements for broad distribution to medical centers around the world. While many technologies exist today to convert the data stream into data packets, intrinsic network limitation and high information contents provided by a multiplicity of required sub-system components stretch the limits of currently available compression technologies. Other technologies that fail to appropriately compress the video screen include Keyboard-Video-Mouse Transmitter/Receiver Pair (KVM) which attempts to send every pixel via the network causing artifacts limiting the quality and refresh rate, so that live medical information can not be properly interpreted. In addition to display information, keyboard, mouse, and other interfaces or input devices data streams should be transmitted in synchrony with the video or graphic data transmission.

Recently, approaches have been proposed to integrate the output data streams of a collection of information sources associated with a complex medical system, such as a minimally invasive navigation system, and to facilitate single-point command and control of the various sub-system information sources through an integrated, combined workstation system comprising image, graphics, and text display and input and command interface means. For example, patent application Ser. No. 11/484,883 entitled "System and network for remote medical procedures" and included by reference in its entirety describes and claims a system with a central control center with controls for each of a plurality of navigation systems, and patent application Ser. No. 11/670,930 entitled "Global input device for multiple computer-controlled medical systems," included by reference in its entirety, describes and claims a composite display with seamless cursor movement. The bandwidth necessary for data transfer from each of the controlled sub-systems to an integrated composite display and control workstation is generally not a limitation, as typically at least one such composite workstation will be located in the vicinity of the complex system and associated sub-systems. However practical and economical means required achieving the objectives described above for training, teaching, proctoring, and other such related objectives, are not currently available.

SUMMARY OF THE INVENTION

The present invention relates to solutions for network bandwidth management in the context of integrated composite display and command workstation. This invention has been developed to enable physicians, call center representatives, and other attendant staff to remotely access multiple live, high resolution displays necessary to monitor and perform medical procedures. The elements of this invention include multiple systems in a lab each with their own display, a consolidated display of the medical systems, at least one converter to translate the local high resolution display into data for transmission over a network, a network link to transmit the data and at least one receiver to compile the data transmitted over the network into a similar high refresh, high resolution display. By consolidating multiple displays into one prior to transmitting over a network, less bandwidth is required and multiple avenues for significant compression, bandwidth reduction, and bandwidth management approaches open-up, as is described below.

More specifically, this invention relates to allocating bandwidth between different sub-systems, taking into account total instantaneous available bandwidth, specific workflow, user preferences, and medical system events. Further, the invention describes systems and methods for the dynamic bandwidth management of a network, comprising a plurality of remote medical field workstations, each field workstation being configured to have the capability to take control of a given intervention as determined by workstation user roles and the dynamic needs of a specific intervention.

Further areas of applicability of the present invention will become apparent from the detailed description provided hereinafter. It should be understood that the detailed description and specific examples, while indicating the preferred embodiments of the invention, are intended for purposes of illustration only, and are not intended to limit the scope of the invention. In particular, while the description focuses on applications to the local or remote control of a complex medical system, it is not so limited.

BRIEF DESCRIPTION OF THE DRAWINGS

The present invention will become more fully understood from the detailed description and the accompanying drawings, wherein:

FIG. 5-A presents a user interface for the allocation of image quality to various windows in a display;

FIG. 5-B shows a different image quality setting retained for the two windows, shown in FIG. 5-A;

Corresponding reference numerals indicate corresponding parts throughout the several views of the drawings.

DETAILED DESCRIPTION OF THE INVENTION

Figure 1:
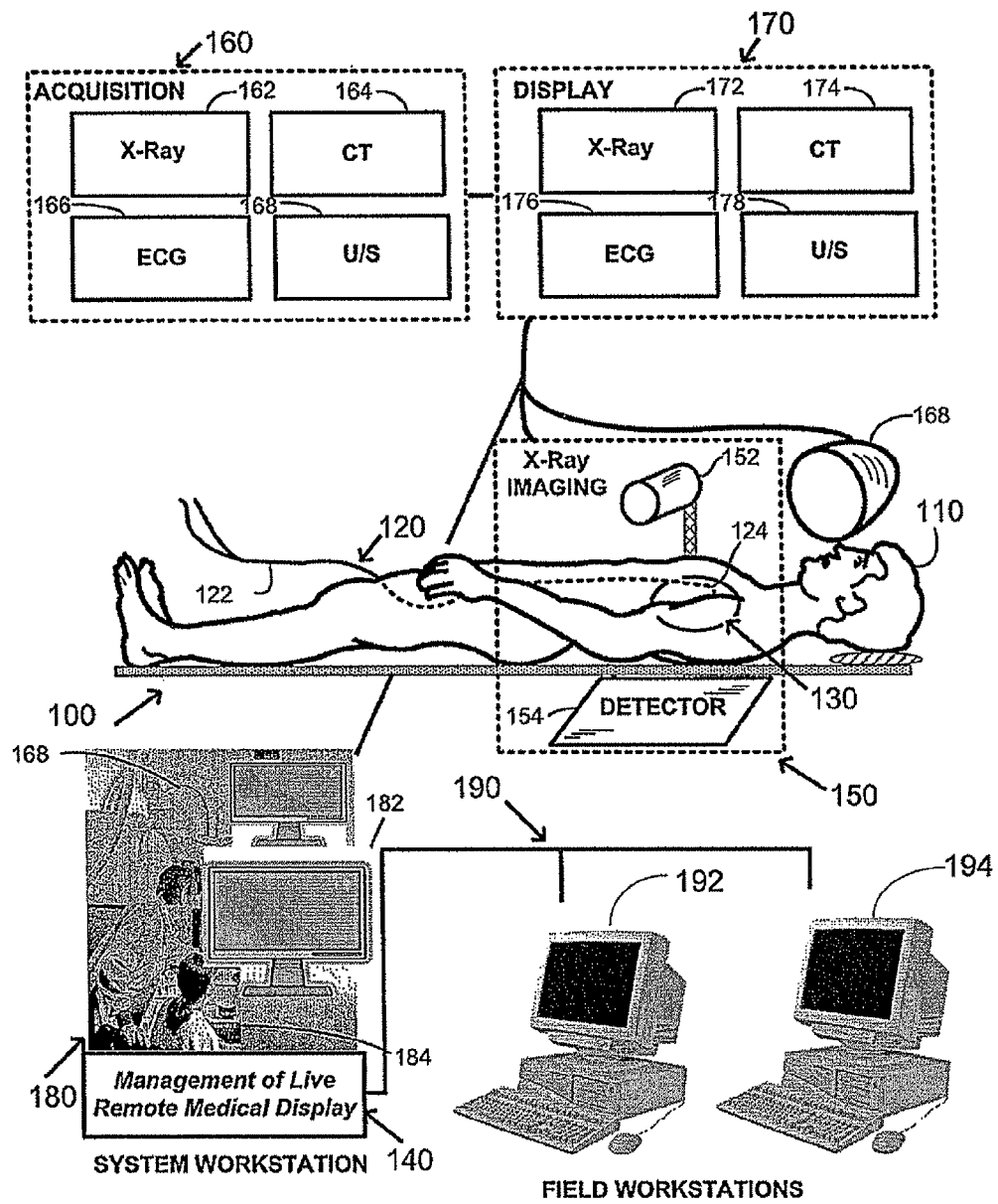
FIG. 1 is a schematic diagram showing a patient positioned in a complex medical system, such as a projection imaging and interventional system comprising a multiplicity of sub-systems, including imaging sub-systems, said complex medical system communicating with a plurality of field workstations through a system workstation connected to a network.

As illustrated in FIG. 1, a patient 110 is positioned within a remotely actuated, computer controlled imaging and interventional complex medical system 100. An elongated navigable medical device 120 having a proximal end 122 and a distal end 124 is provided for use in the minimally invasive interventional system 100 and the medical device is inserted into a blood vessel of the patient and navigated to an intervention volume 130. For illustration of one embodiment, in magnetic navigation a magnetic field externally generated by magnet(s) assembly 168 orients a small magnetically responsive element (not shown) located at or near the device distal end 124. Real-time information is provided to the physician by at least one imaging sub-system 150, for illustration an x-ray imaging apparatus comprising an x-ray tube 152 and a digital x-ray detector 154, to facilitate planning and guidance of the procedure. Additional information acquired 160 may include an electro-cardiogram (ECG) 166, computed tomography imaging (CT) 164, or ultrasound (U/S) data 168, acquired either through a transducer external to the patient or an intravascular U/S probe. The corresponding image data, graph data, and text data are displayed to the physician through displays 172, 174, 176, and 178 each associated to its respective sub-system and shown as a group in display block 170. Alternatively or additionally, other type of data, including image data, are acquired and displayed to the physician, depending on the specifics of the examination underway. As an example, magnetic resonance imaging (MRI) may be used to acquire three-dimensional (3D) anatomy and physiology information about the patient. Many other data acquisition devices, interventional devices, and monitoring systems, as is known in the art, maybe employed in the context of a complex medical system intervention and are understood to be within the scope of this invention. Additionally, FIG. 1 schematically shows block 140 entitled "Management of Live Remote Medical Display" that performs specific functions in various embodiments of the present invention. The medical system described so far is in communication with a system workstation (SWS) 180, which maybe co-located with the medical system 100 or may be located in a separate room. At the system workstation, the communication channels from each separate acquisition sub-system are integrated within one composite display and control system. UIF means are provided for the physician or the assistant to interface and control each of the medical system sub-systems as listed above or as part of the actual complex medical system represented here.

Additionally, the system workstation 180 is in communication with a number of remote field workstations (FWS) 192, 194, . . . , through a network 190. At a given time, or for a given intervention, the roles of these field workstations may vary and assume that of an intervention control workstation, a teaching and training workstation, a support workstation, or a call center workstation, among other possibilities. In the context of this disclosure, the term remote is meant to indicate that the workstation is separate from the displays, UIFs, an controls typically associated with each of the sub-systems described above, such as an x-ray workstation, localization workstation, and so on. A remote workstation maybe located within the complex medical system room, in an adjacent room with view of the medical system, in a central control room within the same medical facility, or miles away at a distant facility.

It is understood that in various embodiments, the functionality of block 140 "Management of Live Remote Medical Display" described herein below may be concentrated within a specific "compression and bandwidth management processor" system, and that such process system may itself be part of the system workstation, or generally may be a component of complex medical system 100; alternatively, the functionality of block 140 may be distributed among various sub-systems, including the system workstation.

In several embodiments of the present invention, a system workstation 180 is associated with the complex medical system, and is the initial point of data and controls management and display. The system workstation configuration may be similar to the remote workstations.

In such embodiment, the system workstation 180 includes the compression and bandwidth management processor and manages the communications from the medical system 100 to remote field workstations, shown as 192 and 194. As the system workstation may itself be remote from the intervention room, it is convenient to distinguish the non-system workstation by labeling them for the purposes of the disclosure "field workstation." It is understood that a field workstation may be physically located in a room adjacent to the system workstation room, or, in specific embodiments, may be co-located next to the system workstation in a single room. The distinction between "system workstation" (SWS) and "field workstation" (FWS) does not, however, mean that the system workstation is always the workstation actually in control of an intervention performed by the medical system 100. Indeed the systems and methods of the present invention are meant in part, to facilitate remote intervention control from one or a plurality of workstation(s) that may be several rooms away in the same building or clinic or a continent apart from the system workstation. A network 190 of limited bandwidth is available for communications between the various system and field workstations. It is clear that in practical embodiments, network communications may occur over a telecommunication wire, a coaxial wire, an RF communication, possibly including satellite links, a fiber optic cable, and other means of high-speed analog and digital telecommunications as known in the art or as may be implemented in the future. Of relevance here, is that the total bandwidth available for each system workstation-to-field workstation communication is limited, and can vary in time due to other load-sharing constraints that may exist within such a network.

Figure 2:
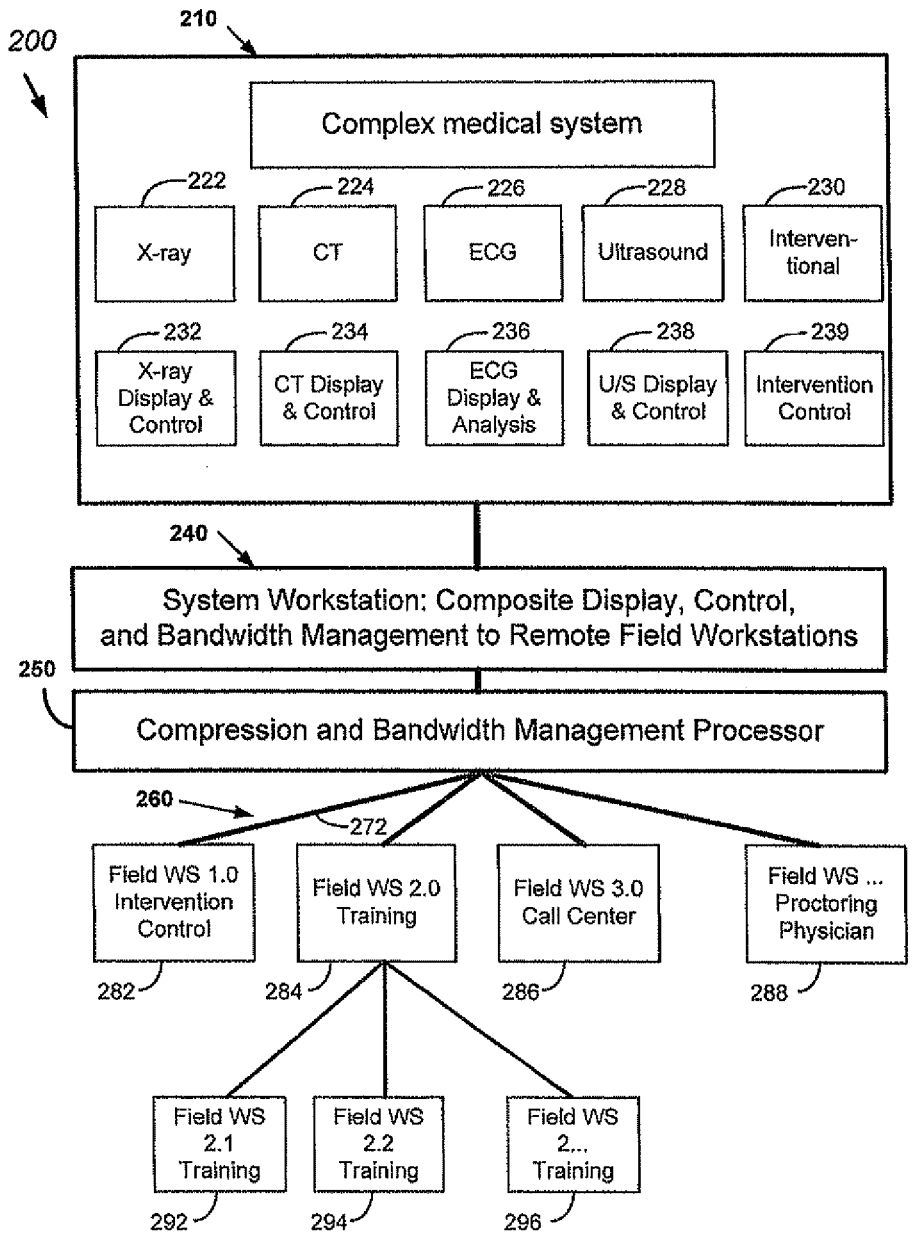
FIG. 2 presents a block diagram of a complex medical system comprising several sub-systems including a multiplicity of imaging sub-systems connected and aggregated into a composite system workstation, the system workstation managing live remote medical display on a number of field workstations.

This invention has been developed to enable physicians, call center representatives and other attendant staff to remotely access multiple live, high resolution displays necessary to monitor and perform medical procedures. One of the challenges addressed herein is to find a way to remotely view a number of high refresh rate, high resolution medical displays via a network with limited bandwidth requirements for broad distribution to medical centers around the world. Referring now to FIG. 2, the elements of this invention designated generally by numeral 200, include multiple sub-systems in a laboratory or medical operating room each with their own display, controls, and UIF, as for example illustrated in FIG. 2: an X-ray imaging system 222 and workstation 232, a CT imaging system 224 and workstation 234, an electro-cardiogram (ECG) system 226 and workstation 236, an ultrasound imaging system 228 and workstation 238, and a minimally invasive interventional system 230 and workstation 239; a consolidated display and UIF control of the medical systems ("system workstation" 240 thereafter) to which substantially all of the sub-systems are connected to and controllable from, at least one converter to translate the local high resolution display into data for transmission over a network 260, a network link 272 to transmit the data and a receiver to compile the data transmitted over the network into a similar high refresh, high resolution display. The at least one converter is part of the compression and bandwidth management processor 250. By consolidating multiple displays into one at the system workstation prior to transmitting over a network, less bandwidth is required. In addition, while many technologies exist today to convert the consolidated high-refresh rate high-resolution display and control data into data packets, a preferred embodiment is one that acquires a snapshot of the display and compresses the display into data that can be transmitted with a sufficient refresh rate to interpret the medical information. In addition to display information, keyboard, mouse, and other interfaces or input devices data can be transmitted while being synchronized with the data transmission of the high resolution display. With this invention, it is now possible to effectively transmit multiple high refresh rate, high resolution displays from a medical lab to remote locations where physicians and other staff can access the information to perform, guide, train and support medical procedures via a cost effective network that can be installed in nearly any medical laboratory. With the network in place, the consolidated display and controls could then be accessed from a call center, office, auditorium or other location. The high refresh, high resolution display could be transmitted from a lab to one location or from a lab to multiple locations, including an intervention control field workstation 282, a training field workstation 284, a call center field workstation 286, a proctoring physician field workstation 288, and other similar field workstations. By sharing the information at multiple locations, live research collaborations, symposia and other events can be effectively hosted over the global medical network. How to attain these and other objects is the subject of the present disclosure.

In FIG. 2, several field workstations, such as the workstation in control of a given procedure, a training workstation, a call center workstation, and a proctoring physician workstation are shown. Additionally, in a layered network configuration, training field workstation 2.0 284 is itself connected to a sub-set of remote training field workstation 292, 294, and 296. Further, although not shown in FIG. 2, more complex topologies, involving more than a single point-to-point workstation communication, may also be present, and are also within the scope of the present invention. For example, there may exist in a subset of workstations, a direct point-to-point connection between each pair of workstations.

A key part of the present invention consists of the bandwidth management for the various network connections. In that regard, the system workstation plays an essential role as interface between the interventional system sub-systems and the other workstations (FWS). The system workstation performs both information source management in the form of data compression and communication channel management through bandwidth allocation and bandwidth management. By monitoring the network, the system workstation measures the bandwidth available for each communication link to a remote field workstation. It also measures the instantaneous amounts of data sent by each of the sub-systems or information sources that it is in communication with. All of the systems and sub-systems described are also in communication to enable information or data flow back from the FWSs to the SWS, and from the SWS to the individual sub-system components that play the roles of major information sources. However in typical embodiments the volume of information flowing back to the SWS and to the individual information sources is small in comparison to that emanating from the information sources and from the SWS toward each of the FWS. Accordingly, the following the description focuses on data flows from the sub-system components to the SWS and from the SWS to the FWSs.

Different sub-systems generate information on a different scale and have different associated "native" bandwidth requirement. Although physical space as counted in number of pixels taken by a window displaying a live x-ray image could be the same as that occupied by a window showing a live ECG, the vector (1-D) dimensionality of the later versus the array (2-D) dimensionality of the former clearly points out that, in general, the bandwidth requirements associated with the live x-ray data are significantly larger. Accordingly, bandwidth allocation takes into account not only the actual display size associated to an information source, but also the intrinsic nature of the sub-system or information source.

The user of the system workstation may choose to allocate bandwidths either on an absolute or relative scale. Absolute bandwidth allocations are appropriate when experimentation has shown that for a given sub-system, below a certain bandwidth threshold meaningful transmission of information becomes compromised. Relative allocations attempt to distribute bandwidth according to workflow, priorities, sub-system intrinsic information contents, user preferences, and available instantaneous channel bandwidth.

The bandwidth allocation is also made dependent on subsystem priorities, either established as part of a protocol or examination workflow, or based on user preferences. An interventional system that includes a live, essentially real-time, endovascular imaging probe will reduce the proportional bandwidth allocation to the x-ray fluoroscopy data, all other parameters remaining the same. A given physician may attribute more weight, that is rely more, on the live fluoroscopic image than to the localization map, even as that later map is being iteratively refreshed. In one embodiment, to each composite display window associated with a specific sub-system, a slider associated uniquely to that window enables the user to manually adjust the amount of bandwidth, and therefore the image or signal quality, associated with that specific sub-system. The user described above would therefore choose a lower proportional bandwidth allocation for the localization map than for the fluoroscopy image, for instance by sliding a cursor on the slider range associated with each window. In a preferred embodiment, this relative bandwidth allocation becomes effective only when the total bandwidth available becomes lower than that required for full-fidelity transmission of all the composite information.

In a preferred embodiment, the initial window bandwidth allocation is determined automatically from design knowledge of the information sources, a combination of intervention-specific protocols, a given user history of preferences and selections, and workflow steps. The slider settings can be absolute or relative; in a preferred embodiment, the slider indicates a relative bandwidth allocation that further weights the allocation as determined by the other parameters listed above. Starting from a bandwidth-starving situation where all sub-systems operate within an allocated bandwidth insufficient for their native bandwidth requirements, as total bandwidth allocation increases for a particular network communication channel linking the SWS to a specific FWS, incremental bandwidth is allocated preferably to the subsystem whose window has the highest relative slider setting; however all linked sub-systems partake in the bandwidth increase, based on a pre-determined formula established from bandwidths parameters described above. Once the highest-priority sub-system bandwidth allocation reaches its native bandwidths, additional increases in bandwidth are allocated to the remaining sub-systems on the priority list.

Similarly, a sub-system that transmits an alert, for instance as based on one of the measured or monitored parameters, would automatically see its total share of the available bandwidth increased in proportion to its increased priority. In remote navigation of medical device, possible events of interest include the tip of a wire or catheter contacting an organ wall or tissue surface; a local ablation area reaching a certain threshold temperature; a locally measured electrical activity and activity lag as compared to a given reference falls below a threshold, and others. Multiple examples will be derived from the particular of an examination, associated diagnostic and or therapeutic goals, and interventional protocols and workflows.

An extreme example of this situation occurs when a medical event is detected and triggers an immediate set of parameter changes to the system control and associated user alarms. The medical event may be detected by simple measures, such as heart rate beat-per-minute, blood oxygen content, or more complex features, such as the detection of ventricular fibrillation. In the case of an ablation procedure, power delivery to the ablative instrument automatically stops.

Specific examination workflows are associated to specific default relative or absolute bandwidths allocations. In a preferred embodiment, a history of user preferences is built and the system workstation learns such preferences in the context of particular workflows. By design a "safe-mode" is provided should absolute bandwidth decrease between a specific remote FWS or set of remote workstations: for example, an intervention controlling workstation, at which an expert or proctoring physician is located. In such a situation, urgent communication messages are displayed, intervention steps are delayed and/or control is returned to either the SWS or a FWS with minimum bandwidth allocation sufficient for safe intervention progression. The SWS continuously monitors bandwidth allocations between FWS and in a fail-safe mode is capable of redirecting bandwidth away from secondary role FWS to the control FWS to allow for continued safe intervention.

As will be described in more details below, the specific architecture of the system considered in its entirety, comprising a first set of sub-systems that are all combined at a system workstation, and then a combined data stream from the workstation to the field workstation, enable a multi-layer approach to data compression. More specifically, at least four different compression levels or layers can be identified, and are now described in turn.

Figure 3:
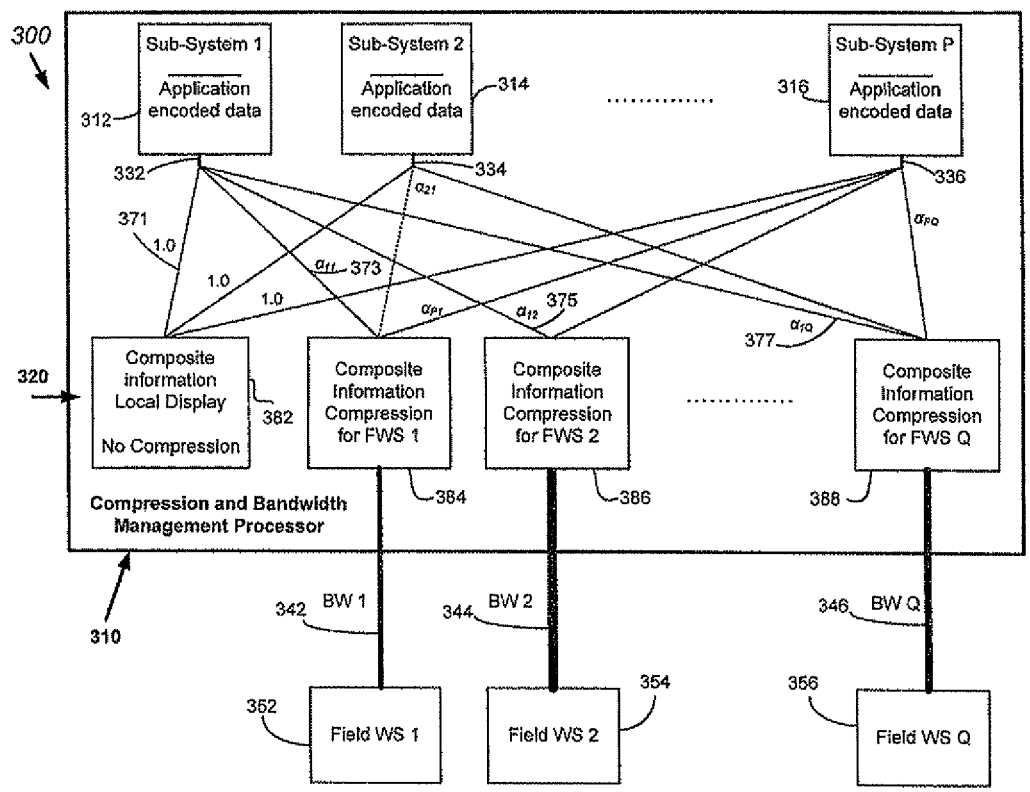
FIG. 3 presents in more detail, the first two compression and bandwidth management layers disclosed in the present invention.

The first two compression and bandwidth management layers are described schematically in FIG. 3, and referred generally by numeral 300. In a first layer of compression, the data from each sub-system 312, 314, . . . , 316 may be compressed or encoded at the sub-system level, prior to transmission to the system workstation. As illustrated, it is common in x-ray imaging to acquire data on a 16 or more bit depth; as a result the acquire image data have a dynamic range of up to $2^{**}16$ or 65,536 gray levels, well beyond the gray scale dynamic range of most display monitor (typically at about 8 bits or 256 gray levels). Accordingly most x-ray systems provide an image gray scale compression algorithm. The resulting images ("For Presentation" in DICOM parlance) allow the user to essentially view all or most of the information of importance in the full original dynamic range, while the "For Presentation" data are coded on 8-bits. Thus a factor 2 compression is typically available from such image presentation algorithms. Other specific modalities also have specific "intrinsic" compression algorithms that are used routinely without loss of diagnostically relevant information. It is emphasized here that this level of compression and image enhancement is not necessarily a one-to-one reversible compression. Depending on the application type, the amount of compression considered clinically acceptable varies. For a projection x-ray image used in a diagnostic setting, a factor two dynamic range compression is typically acceptable.

In a key aspect of the present invention, specific bandwidth management steps and compression methods retained may be dependent upon which field workstation, or subset of field workstations, the data is intended to be sent to. As different users and different roles may accommodate or accept varying amount of compression and variable styles of bandwidth allocation, data transmission from the system workstation to the field workstations is optimized on a field workstation (or field workstation subset) basis. In such an embodiment, as represented schematically in FIG. 3 by arrow 320, appropriate computer power is provided within the compression and bandwidth management processor to account for the various end-user needs, number of field workstations, communication pipes bandwidths available, and associated bandwidth management approaches. There, and dependent upon the bandwidth available to the system workstation, the relative priorities allocated by the particular user to the various sub-systems, and the specific workflow requirements of the present invention, the various sub-system data streams are weighted as described above and combined in a set of virtual composite images 384, 386, . . . , 388 to be transmitted to respective remote field workstations 352, 354, . . . , 356. In most instances, the virtual composite data are not actually displayed at the SWS. Instead uncompressed composite data 382 are generated for display on the system workstation. The meaning of the term "weight" here is that depending upon the relative weight, the sum of the individual sub-system bandwidth requirements, and the total bandwidths available for each communication channel between the SWS and each FWS (or FWS subset or group), the amount of compression necessary for each of the sub-system is determined. This determination is done on a FWS or communication channel basis, and accounts for the instantaneous bandwidth $BW_1$ 342, $BW_2$ 344, . . . , $BW_Q$ 346, available at a given time for communications between the system workstation 310 and each of the remote field workstations 1 352, 2 354, . . . , Q 356. The determination proceeds in two steps. First, the sum of the total sub-system bandwidth requirements is divided into the channel bandwidth available for a specific channel. If the resulting ratio R is greater or equal to 1.0 (uncommon in bandwidth limited network) no compression is necessary. For R<1.0, the bandwidth is allocated to each sub-system in function of their normalized priority, as normalized to sum to R. As will be seen below, the ratio R is also normalized for residual compression and bandwidth management gains that can be achieved by compression layers 3 and 4. Thus, in a second level of compression, each data stream 332, 334, . . . , 336 from each subsystem 312, 314, . . . , 316 is compressed in function of its compression weight; the resulting images and data are then combined in an aggregate image that is equal to that that will be seen by the end user of the FWS considered. Accordingly, each input data stream is potentially compressed at Q different levels, where Q is the number of target or destination FWSs. For illustration, data stream 332 from sub-system 312 is allocated weights 1.0 371, $\alpha_{1,1}$ 373, $\alpha_{1,2}$ 375, . . . , $\alpha_{1,Q}$ 377, respectively for the local system workstation display, remote field workstations 1 352, 2 354, and Q 356, respectively.

In another aspect of the present invention, the system workstation tracks commands or inputs from the user, and based at least partially on such inputs, modifies bandwidth allocation. As the system workstation provides a composite display, more information than can typically be viewed by a single user at any given time is presented. Accordingly at any point during an intervention, the user dynamically focuses on specific sub-systems through their associated display windows on the composite display. This and subsequent compression and bandwidth management layers are described in FIG. 4, generally denoted by numeral 400. Determination of which sub-system(s) is/are at the user's focus of attention is done in level 3 410 by a combination of means, including mouse inputs, cursor position adjustments, keyboard inputs, or voice inputs. In one embodiment, the user controls a cursor via an input, such as a mouse or joystick, and the cursor position on the screen indicates the focus area center. Alternatively or additionally, other user input commands, such as typed commands, menu selections, or voice commands serves to direct or influence the selection of the user area of focus. A learning tool is provided on the workstation, so that the history of user preferences with respect to focus areas and windows layout is recorded and learnt by the system. In a training mode, a user may be prompted by a voice recording or text output to focus in specific areas of the display as a function of the current step in a workflow.

Additionally in one embodiment, a means is provided at one or more workstation to track the user's eye motion. As the user is actively viewing or focusing on one area of the display, software assisted by detection means including user position sensor means and an eye-position tracking device identify the user's area of focus on the screen. The software design accounts for the rapid eye side motions that user viewing a computerized display typically experience; averaging and filtering of the eye position allows the definition of a dynamic, but relatively slowly varying area of focus.

In one embodiment, separate sub-systems windows layouts are rearranged dynamically as a function of the workflow, so that a cluster of windows provides a region of interest (typically centered on the display), wherein substantially all of the step-relevant information is found, facilitating the user focusing on the most relevant information source while maintaining secondary relevant sources in the near neighborhood of the main window. In such embodiment, according to user preferences, such dynamic layout redistribution may occur automatically, may occur only after user acceptance following a prompt (such as a voice prompt), or not occur at all. Further, several modes of layout transitions are provided that are also the object of user selection (in analogy with transition modes between slides in a PowerPoint presentation).

In any of the above described user focus center area determination means, or for any similar determination means, a focus area is determined and that determination in turn, serves as an input in the bandwidth management and compression algorithm approaches. The center focus area is allocated proportionally more bandwidth as compared to the surrounding areas. Transition between these center and surrounding areas may be effected in a linear or non-linear manner; and maybe relatively marked or, in the limit, non-existent.

In one embodiment, spatially encoding data with a center focus comprises sampling the data on a radial grid centered at the focus point. Accordingly, the density of samples is the highest at the focus center and decreases linearly with distance from the center.

Figure 4:
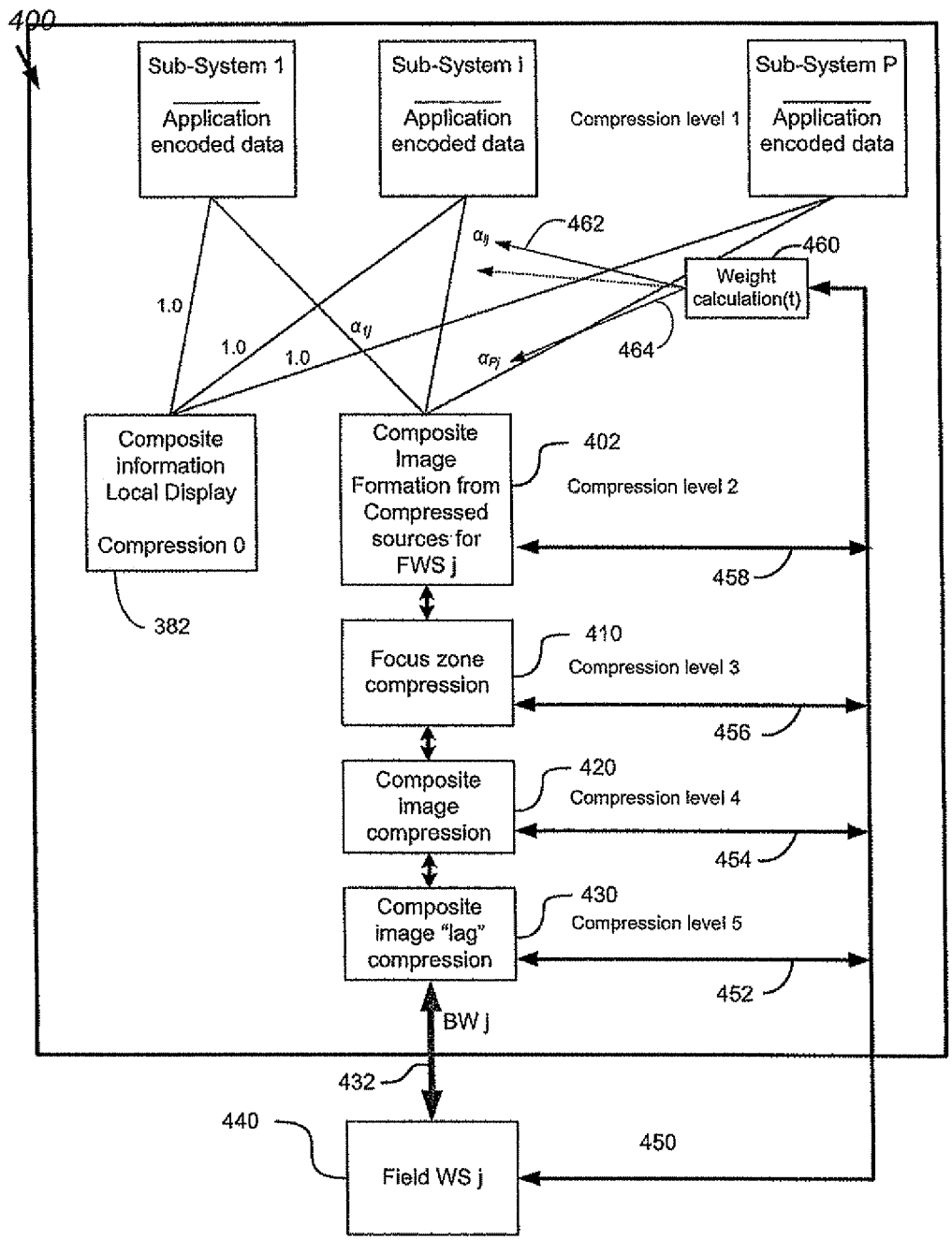
FIG. 4 additionally describes compression and bandwidth management layers 3, 4, and 5, disclosed in the present invention.

Thus, and referring to FIG. 4, a third layer of compression 410 is identified by dynamically defining an instantaneous region of focus, and surrounding regions, and by compressing the aggregate (combined) data accordingly. In one embodiment, the output of the third layer of compression is equal to the composite image data that is presented to the user of a specific FWS. It is noted that compression and bandwidth management layer 410 may both work directly with the individual sub-system data streams, or with an aggregate as seen by user around a focus center point. Direct source data encoding according to this layer may lead to an image quality that generally decreases away from the focus center, the spatial variation being sub-system data stream window-dependent, rather than dependent upon the distance from the focus center point. In comparison, a simple radial spatial encoding, as described above will lead to a spatial variation that depends directly upon the distance from the user center of focus.

In a fourth layer of compression denoted by 420 in FIG. 4, the output of the third compression layer is compressed using video or image compression techniques, as known in the art. Approaches derived from the MPEG standard and similar are applicable to the composite output of the third compression step. Typically this compression step can also be chosen to be lossless, or to be performed at an overall level of loss acceptable to the user. In lossless compression, an inverse compression step takes place at the FWS prior to presentation.

In a preferred embodiment, further bandwidth gains are achieved by using both spatial and temporal compression method, whereby bandwidth is allocated both based upon spatial and temporal resolution considerations. In one embodiment, both the spatial and temporal resolution of the data away from the user focus center are reduced as compared to the focus center. Alternatively, define different spatial horizons with different spatial/time resolution trade-offs. That is, the time sampling frequency is spatially dependent; or stated conversely, the spatial resolution is also a function of the time resolution. This compression and bandwidth management layer is represented schematically by block 430 in FIG. 4, although it is recognized that the associated functionality may be distributed among different layers in various embodiments.

In a typical intervention involving several users with a subset of users at a set of remote workstations, roles are typically assigned for all or most of the intervention to the different users. Control of the intervention is within the hands of the intervening physician; occasionally a mentoring physician or expert may for a few moments or for more extended period of times, be in control of the interventional system. In any case, a limited subset of users is actually in control of the intervention, and other users are present in a more limited role. For this subclass of user, it might be in general, acceptable to provide either a somewhat reduced spatial or temporal resolution. Alternatively it is acceptable to provide a restored image quality at the cost of a small lag in the presentation of images and data. In such a situation, and for the subclass of users who don't need real-time data, send high spatial resolution at a low frame rate, and up-interpolate temporally between the frames: introduces a bit of a lag, of the order of 1 or a few seconds. There composite images are sent at a high-spatial resolution, but a reduced frame rate. Images are up-interpolated at the receiving workstation 440, to provide the user with a smooth flowing viewing experience. Accordingly, this defines a fifth level of compression denoted by 430 in FIG. 4, using lag as a dimension to interpolate temporal data for subsequent presentation.

Thus in a general sense, the three parameters available for data compression and bandwidth management: 1) spatial resolution; 2) temporal resolution; 3) amount of lag acceptable. As seen above, these parameters are in general considered in combination, and in the context of this disclosure referred to individually or in various combinations as information coding methods.

Compression levels two to five, and in particular, compression levels two, three, and five, depend upon specific parameters set by the user(s) of the receiving workstation 440. Accordingly, communications means 450 is provided for parameter and feedback information communication from the remote field workstation to each of the compression levels, as shown respectively by arrows 452, 454, 456, 458, and 460. Focusing in particular on block 460, showing the weights calculations for compression and bandwidth management level two, and as described above, the compression weights 462, . . . , 464 depend on the workstation role, user preferences, user focus center, bandwidth available, and so forth as described previously. Further, as indicated in block 460, these calculations are dynamic as most if not all of these parameters may vary over the course of one medical system intervention.

In a typical interventional system embodiment, most sub-systems generate data at a predictable rate. As an example, the data rate for an x-ray fluoroscopy sequence is given by the image size and pixel digitization depth, data acquisition rates, and apart from being turned on or off, is unlikely to change over time. This provides a convenient means to monitor the information content of each source, by comparing the nominal information rate to the actual information rate achieved by compressing each source data stream. Accordingly, a means is provided for each sub-system to monitor its relative information rate and absolute bandwidth needs as a function of time. The compression and bandwidth management processor thus knows of these absolute and relative bandwidth requirements and can reallocate bandwidth over time as the information source requirements change. Alternatively or additionally to the comparative means proposed above, other means of calculating the absolute and relative bandwidth requirements of an information source may be used, as is know in the art. The absolute and relative bandwidth requirements of an information source are then taken into account by the system workstation in generating a field-workstation-dependent bandwidth management.

As illustrated schematically in FIG. 5, in one particular embodiment, each FWS user has control of the relative image quality to be associated to each sub-window and corresponding data acquisition sub-system. Based on a history of user preferences, pre-allocated bandwidth levels are applied to the various display windows. In FIG. 5-A, data and image windows 502 and 504 are assigned respective image quality levels through cursors 512 and 514, clearly emphasizing window 502 over window 504. This level of image quality may be preset, as described above, or maybe dynamically set based on user focus or system events or intervention priorities. In FIG. 5-B, possibly due to changes to the dynamic of the intervention, or by the user directly adjusting the cursor levels associated with the window, the image quality emphasis has shifted to window 524 over window 522, as shown by respective image quality or bandwidth allocation cursors 532 and 534.

Figure 6:
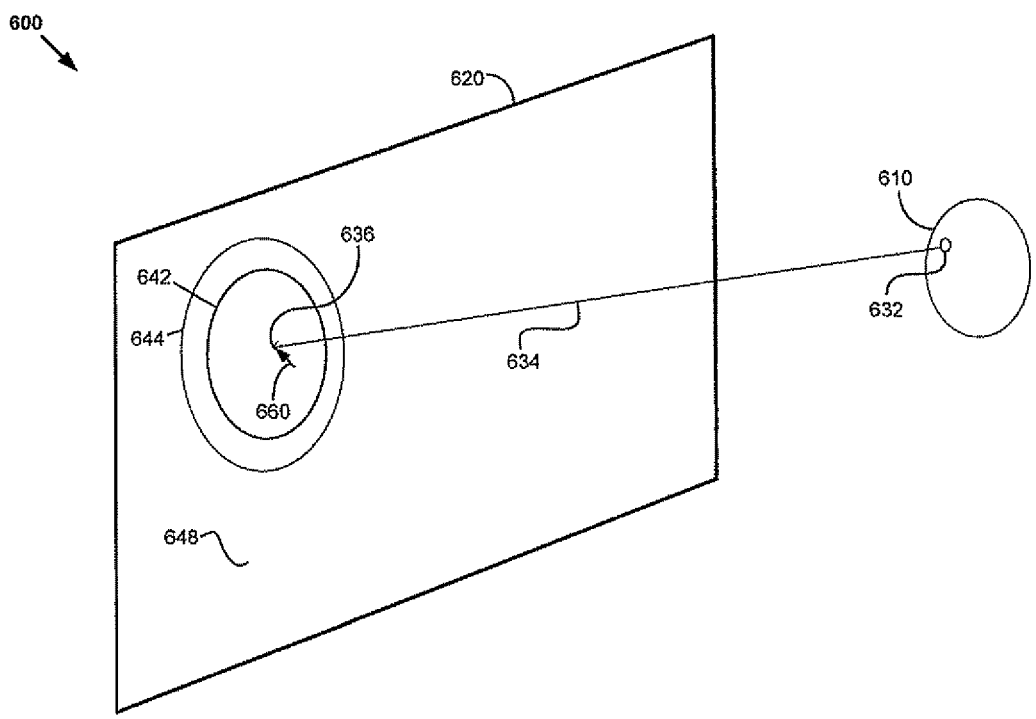
FIG. 6 illustrates schematically a method of determining a user center of focus through an eye tracking device or through a UIF-driven cursor.

FIG. 6 schematically illustrates dynamic determination of a FWS user's focus center. User 610 is observing composite display 620 of the remote field workstation. An eye-tracking device located at or near the display (not shown), tracks the user's eye focus 632, and determines an associated line-of-sight 634 based on known geometry and determined user distance from the display, and corresponding focus zone center 636 on the display. A primary zone of focus 642, is automatically computed and its location and size parameters transmitted back to the system workstation for adjustment of the dynamic compression and bandwidth management parameters, such that zone 642 is associated with the highest relative image quality. A transition zone 644 is also automatically determined based on a history of user preference and FWS settings, and correspondingly image quality is gradually adjusted from the center focus zone 642 to a "background" zone 648 essentially comprising the remainder of the display. Additionally or alternatively, a cursor 660 is manually positioned by the user through a joystick or other UIF device associated with the FWS, and defines the center of the focus region 642.

It is common for physicians during an intervention to review data to ascertain the progress of the procedure, and ensure that the desired results have been achieved. One form of review consists of looking at image data sequence acquired after a specific intervention step. In one embodiment of the present invention, error data sequence are collected and measured on the encoding (system) workstation; the error being defined as the difference between the uncompressed data being presented and displayed at the system workstation and the data being transmitted to a specific field workstation; it is therefore FWS-specific. Although total network allocated bandwidth might vary slowly, it is reasonable to expect that the composite display, or at least sub-components thereof, will see fast temporal variations. Accordingly, when the bandwidth requirements fall, or conversely when the amount of available bandwidth increases, the past error sequences are automatically sent to one or a set of field workstations, and a sequence of exact image sequences is reconstructed in the background at those FWSs. Should the user/physician reach a point where image review is necessary, it becomes possible to then present at least part of a past sequence of images at full, native, image quality. This facilitates the physician review, and provides the best available image quality for monitoring the effect of the intervention up to now and controlling the intervention next steps.

Operation

Figure 7:
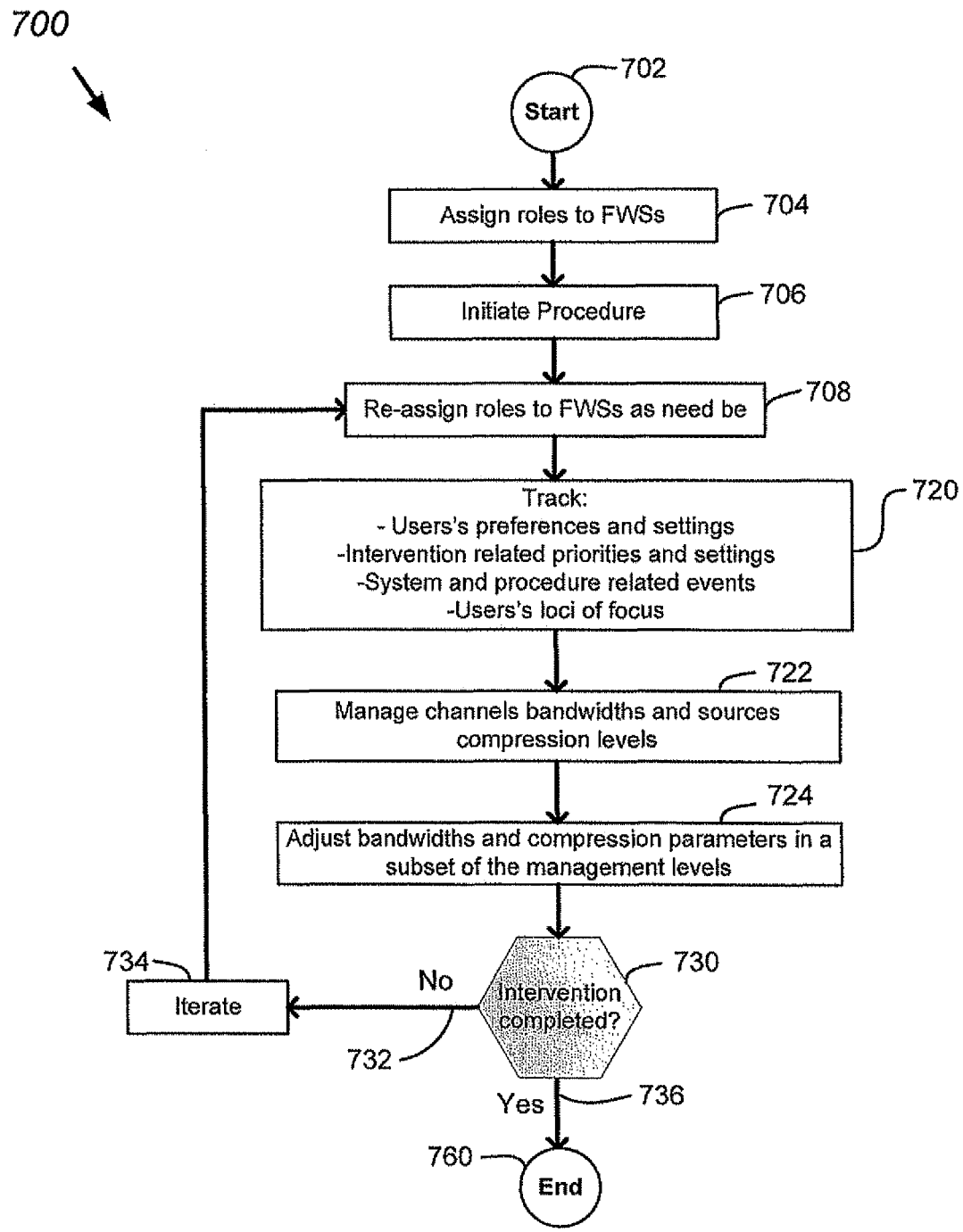
FIG. 7 presents a flow chart of a preferred embodiment of the as applied to the complex medical system of FIG. 1.

An exemplary workflow of the systems and methods of one embodiment of the present invention is described schematically in FIG. 7. Upon the start of an intervention, 702, specific roles are assigned to various FWSs, step 704. The procedure is then initiated, step 706, and if need be roles are re-assigned in step 708. In step 720 the FWSs track the users' preferences and settings, the intervention-related priorities and settings, and these information sets are communicated to the system workstation, which, based in part upon those data as well as specifics of the procedures and user events, calculates levels of compression and bandwidth allocations for each of the FWSs. These initial management decisions are dynamically tracked and modified as a function of the intervention needs and of each FWS user's focus of control, step 722. The corresponding compression levels and bandwidth allocations are assigned to the respective information sources and communication channels through one or more of the compression and bandwidth management levels described above, step 724. At decision point 730, should the intervention not be completed 732, the method iterates through block 734 back to FWSs user role assignments, as necessary, tracking of the various data streams and user settings and priorities, till the intervention completes, step 736, and the method terminates, 760.

The advantages of the above described embodiments and improvements should be readily apparent to one skilled in the art, as to enabling bandwidth management and compression levels determination for the transmission of complex, composite sub-system data over a network of limited bandwidth to a set of remote users at a number of field workstations. Additional design considerations may be incorporated without departing from the spirit and scope of the invention. Accordingly, it is not intended that the invention be limited by the particular embodiments or forms described above, but by the appended claims.

What is claimed is:

1. A method of locally displaying multiple items of medical information from at least one remote medical system having an output display, the method comprising:
   assembling the multiple items of medical information from the output display of at least one remote medical systems into a composite display having regions corresponding to the multiple items of medical information; and
   communicating video data for the composite display to a local display over a network by a computer, differentially treating the video data corresponding to the regions by transmitting the video images for selected regions of the composite display at different resolutions than the video images for other regions.

2. A method of locally displaying multiple items of medical information from at least one remote medical system having an output display, the method comprising:
   assembling the multiple items of medical information from the output display of at least one remote medical systems into a composite display having regions corresponding to the multiple items of medical information; and
   communicating video data for the composite display to a local display over a network by a computer and preferentially allocating network transmission bandwidth to the video data corresponding to selected regions of the composite video display, wherein the network transmission bandwidth is allocated among the regions of the composite display based at least in part upon the medical systems currently being used, which is determined by detecting the region that the user is looking at.

3. A method of locally displaying multiple items of medical information from at least one remote medical system having an output display, the method comprising:
   assembling the multiple items of medical information from the output display of at least one remote medical systems into a composite display having regions corresponding to the multiple items of medical information; and
   communicating video data for the composite display to a local display over a network by a computer and selectively applying different methods and/or different degrees of compression to the video data corresponding to selected regions of the composite video display, the method or degree of compression being determined for the video data for the regions of the composite display based at least in part upon the medical systems currently being used, determined by detecting the region that the user is looking at.

4. A method of locally displaying multiple items of medical information from at least one remote medical system having an output display, the method comprising:
   assembling the multiple items of medical information from the output display of at least one remote medical systems into a composite display having regions corresponding to the multiple items of medical information; and
   communicating video data for the composite display to a local display over a network by a computer and selectively applying different information encoding to the video data corresponding to selected regions of the composite video display, by applying different resolution to the video data.

5. A method of locally displaying multiple items of medical information from at least one remote medical system having an output display, the method comprising:
   assembling the multiple items of medical information from the output display of at least one remote medical systems into a composite display having regions corresponding to the multiple items of medical information; and
   communicating video data for the composite display to a local display over a network by a computer and selectively applying different information encoding to the video data corresponding to selected regions of the composite video display, wherein the information encoding is for at least one selected from the group consisting of resolution, bandwidth, and compression, wherein the different information encoding for the video data for the regions of the composite display is determined based at least in part upon the medical systems currently being used by detecting the region that the user is looking at.

* * * * *